June 18, 1974 W. A. WARRINER Plant Pat. 3,571
ROSE PLANT
Filed Jan. 8, 1973
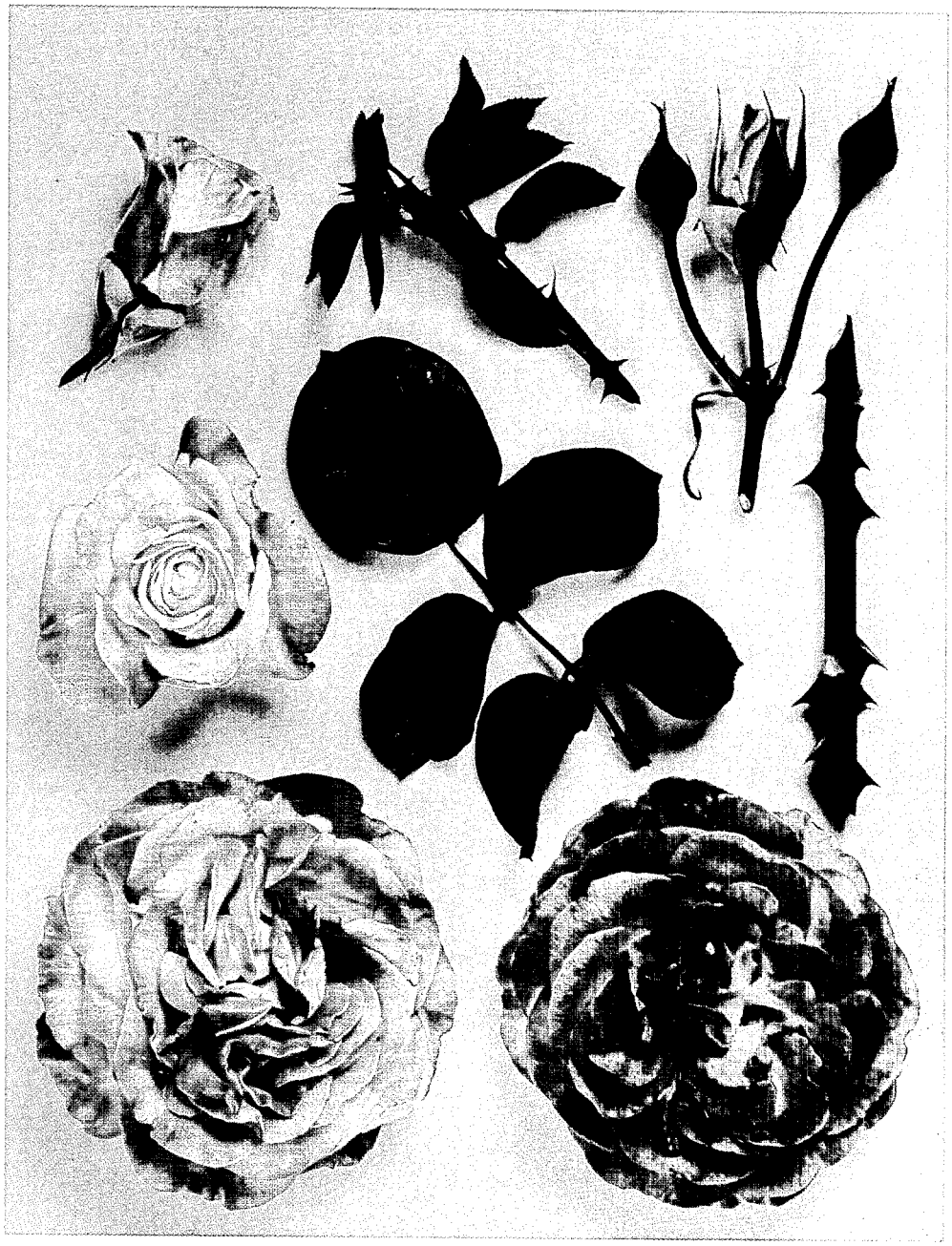

United States Patent Office

Plant Pat. 3,571
Patented June 18, 1974

3,571
ROSE PLANT

William A. Warriner, Tustin, Calif., assignor to Jackson & Perkins Company, Medford, Oreg.

Filed Jan. 8, 1973, Ser. No. 321,717
Int. Cl. A01h 5/00
U.S. Cl. Plt.—11 1 Claim The present invention relates to a new and distinct variety of rose plant of the hybrid tea class which was originated by me by crossing the variety South Seas, U.S. Plant Pat. 2,184 with pollen from an unnamed, undistributed hybrid tea variety.

The primary objective of this breeding was to produce a new rose variety of the hybrid tea class, combining the good plant characteristics of the seed parent with the unusual flower color of the pollen parent. This objective was substantially achieved along with other desirable improvements as evidenced by the following unique combination of characteristics which are outstanding in the new variety and which distinguish it from its parents as well as from all other varieties of which I am aware:

1. A vigorous, upright habit of growth.
2. Large dark green foliage.
3. Heavy canes and stems mostly of a Garnet Brown color.
4. A novel blend of color and a photosensitivity more pronounced than in most hybrid tea varieties.
5. Colors range from Maize Yellow (Wilson) in petals exposed very little to sunlight to a deep chrysanthemum crimson (Wilson) after a day or two exposure to sunlight.
6. Little or no fragrance.

Asexual reproduction of this new variety by budding, as performed as Wasco, California, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with *Wilson's Horticultural Color Chart,* except where ordinary dictionary significance of color is indicated.

Percentage: Seedling.
*Seed parent.*—South Seas, U.S. Pl. Pat. 2,184.
*Pollen parent.*—Unnamed variety.
Classification:
*Botanic.*—Rosa hybrid.
*Commercial.*—Hybrid Tea.

FLOWER

Observations were made at Irvine, Calif., in mid-October in the afternoon of plants and blooms from garden.
Blooming habit: Recurrent—continuous.
Bud:
*Size.*—One inch to 1¼ inches when petals start to unfurl.
*Form.*—Pointed, oval.
*Color.*—When sepals first divide lighter than Oxblood Red (00823/3). One-fourth blown: Upper side Maize Yellow (607/3) irregularly overlaid with Spinel Pink (0625). Lower side: More heavily overlaid with Spinel Pink (0625). When half blown; inside of petals, outer half near Rose Opal (022). Center area remains near Maize Yellow (607/3), reverse of petals mostly near Rose Opal (022) with irregularly shaped areas of Maize Yellow (607/3).
*Sepals.*—Color: Outer surface—Scheeles Green (860/3). Inner surface—Lighter than Scheeles Green (860/3) with a light covering of white tomentum. Three appendaged sepals lightly appendaged. Two unappendaged sepals hairy-edged.
*Receptacle.*—Color: Scheeles Green (860/1). Shape: Funnel. Size: Large, long. Surface: Slightly hairy, a few stipitate glands.
*Peduncle.*—Length: Medium. Surface: Few stipitate glands, slightly hairy. Color: Bronzy on side toward sun. Strength: Stiff, erect, heavy.
*Opening.*—Open slowly. Petals curling very little, mostly folding out.
Bloom:
*Size.*—Large. Average size when fully expanded approximately 4 to 5 inches.
*Borne.*—Singly, occasionally in clusters.
*Stems.*—Long, strong.
*Form.*—When first open, high center. Performance—retains its form until the end.
*Petalage.*—Number of petals under normal conditions 40 to 50.
*Color.*—Center of flower: Upper side of petals—As flower opens color deepens from a light overlay of Spinel Pink (0625) to Chrysanthemum Crimson (824/3) with only irregular areas retaining the Maize Yellow (607/3) color. Reverse side of petals retain Maize Yellow (607/3) over most of area with overlay of Spinel Pink (0625). Outer petals: Upper side of petals are exposed to sun longer, therefore develop the darker Chrysanthemum Crimson (824/3) sooner. Reverse of petals lose Maize Yellow as it fades to near white overlaid with Spinel Pink (0625). Base of petals Primrose Yellow (601). General tonality from a distance Maize Yellow (607/3) overlaid with Spinel Pink (0625) in early stages to Chrysanthemum Crimson (824/3) in fully open stages. No varigations.
*Discoloration.*—As flower opens, color increases in intensity on upper side of petals to Chrysanthemum Crimson (824) where exposed to sun. Under side of outer petals and areas covered with petals fade to near white with overlay of Spinel Pink (0625). Color changes faster on warm summer days. In cool weather (spring and fall) several days are necessary to develop the change to Chrysanthemum Crimson.
*Fragrance.*—Slight.
Petals:
*Texture.*—Thick.
*Surface.*—Inside—satiny. Reverse—satiny.
*Shape.*—Round.
*Form.*—Tips slightly recurved.
*Arrangement.*—Imbricated.
*Petaloids in center.*—Few.
*Persistence.*—Drop off cleanly.
*Lastingness.*—On the plant—long. As cut flower—long.
Reproductive parts:
*Stamens, anthers.*—Large. Color—Yellow. Arrangement—regular around styles.
*Stamens, filaments (threads).*—Assorted. Color—reddish.
*Pollen.*—Gold yellow.
*Styles.*—Loosely separated. Short, medium, long.
*Stigmas.*—Color—white.
*Ovaries.*—All enclosed in calyx.

PLANT

Form: Bush.
Growth: Very vigorous.
Foliage: Number of leaflets on normal mid-stem leaves, 5, sometimes 7.
*Size.*—Very large.
*Quantity.*—Abundant.
*Color.*—New foliage: Near Garnet Brown (00918/3).—Old foliage: Parsley Green (00962).
Leaflets:
*Shape.*—Broad, oval.
*Texture.*—Upper side semi-glossy. Under side rough with veining. Ribs and veins, prominent.
*Edge.*—Serrated.
*Serration.*—Single, small.
*Petiole.*—Rachis—Color—near Garnet Brown on upper side, Scheeles green below. Underside—Few large prickles, slightly hairy.
*Stipules.*—Medium.
*Disease resistance.*—Resistant to mildew under normal growing conditions at Irvine, Calif.
Wood:
*New wood.*—Color—Garnet Brown (00918/3). Bark—smooth.

*Old wood.*—Color—Garnet Brown (00918/3). Bark—smooth.
Prickles:
*Quantity.*—On main stalks—ordinary. On laterals—ordinary.
*Form.*—Broad base, long, hooked downward.
*Color.*—When young—red.
*Position.*—Irregular.
Small prickles:
*Quantity.*—On main stalks—few. On laterals—few.
*Color.*—Brown.

I claim:

1. A new and distinct variety of rose plant of the hybrid tea class, substantially as herein shown and described, characterized particularly as to novelty by the unique combination of its dark semi-glossy, abundant foliage; vigorous, upright habit of growth; Maize Yellow bud color which, upon exposure to sunlight, changes into a deep Chrysanthemum Crimson.

No references cited.

ROBERT E. BAGWILL, Primary Examiner